(12) United States Patent
Burkhardt et al.

(10) Patent No.: US 8,969,045 B2
(45) Date of Patent: Mar. 3, 2015

(54) METHOD FOR DETECTING PYROPHOSPHATE BY MEANS OF BIOLUMINESCENCE DETECTION

(75) Inventors: Nils Burkhardt, Velbert (DE); Stefan Heitmeier, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 1377 days.

(21) Appl. No.: 12/515,218

(22) PCT Filed: Nov. 7, 2007

(86) PCT No.: PCT/EP2007/009625
§ 371 (c)(1),
(2), (4) Date: Dec. 23, 2009

(87) PCT Pub. No.: WO2008/061626
PCT Pub. Date: May 29, 2008

(65) Prior Publication Data
US 2010/0092966 A1    Apr. 15, 2010

(30) Foreign Application Priority Data

Nov. 20, 2006  (DE) .......................... 10 2006 054 562

(51) Int. Cl.
*C12P 19/34*  (2006.01)
*C12Q 1/66*  (2006.01)

(52) U.S. Cl.
CPC ...................................... *C12Q 1/66* (2013.01)
USPC ...................................................... 435/91.2

(58) Field of Classification Search
USPC ...................................................... 435/91.2
See application file for complete search history.

(56) References Cited

U.S. PATENT DOCUMENTS

| 3,520,660 A * | 7/1970 | Hoffman et al. ............ 435/287.3 |
| 5,814,471 A * | 9/1998 | Wood ................................. 435/8 |
| 6,913,898 B2 * | 7/2005 | Schindler et al. ................. 435/8 |
| 2005/0112601 A1 * | 5/2005 | Hassibi et al. .................... 435/6 |

FOREIGN PATENT DOCUMENTS

| DE | 19602662 | 8/1997 |
| EP | 1793002 | 6/2007 |
| WO | WO 2006/013837 | 2/2006 |

OTHER PUBLICATIONS

Fontes et al., Biochemical and Biophysical Research Communications, vol. 237, pp. 445-450, 1997.*
McElroy, W.D., et al., The Mechanism of Action of Pyrophosphate in Firefly Luminescence, Archives of Biochemistry and Biophysics, vol. 46, Isssue 2; 1953; pp. 399-416.
Ahmad, M., et al., Analytical Aspects of the Firefly Luciferase Reaction Kinetics, Intl. Symp. Anal. Appl. Biolumin. Chemilumin, $2^{nd}$., 1980, pp. 435-441.
Ronaghi, M., et al., Real-Time DNA Sequencing Using Detection of Pyrosphosphate Release, Analytical Biochemistry, vol. 242, 1996, pp. 84-89.

* cited by examiner

*Primary Examiner* — Cynthia B Wilder
(74) *Attorney, Agent, or Firm* — Thomas C. Blankinship

(57) ABSTRACT

The invention relates to methods for detecting pyrophosphate by means of bioluminescence detection. In addition, methods for measuring chemical, especially enzyme-catalyzed, reactions in which pyrophosphate is formed or consumed are described. Such reactions are catalyzed for example by guanylyl cyclases, adenylyl cyclases, DNA polymerases or RNA polymerases.

Figure 1:
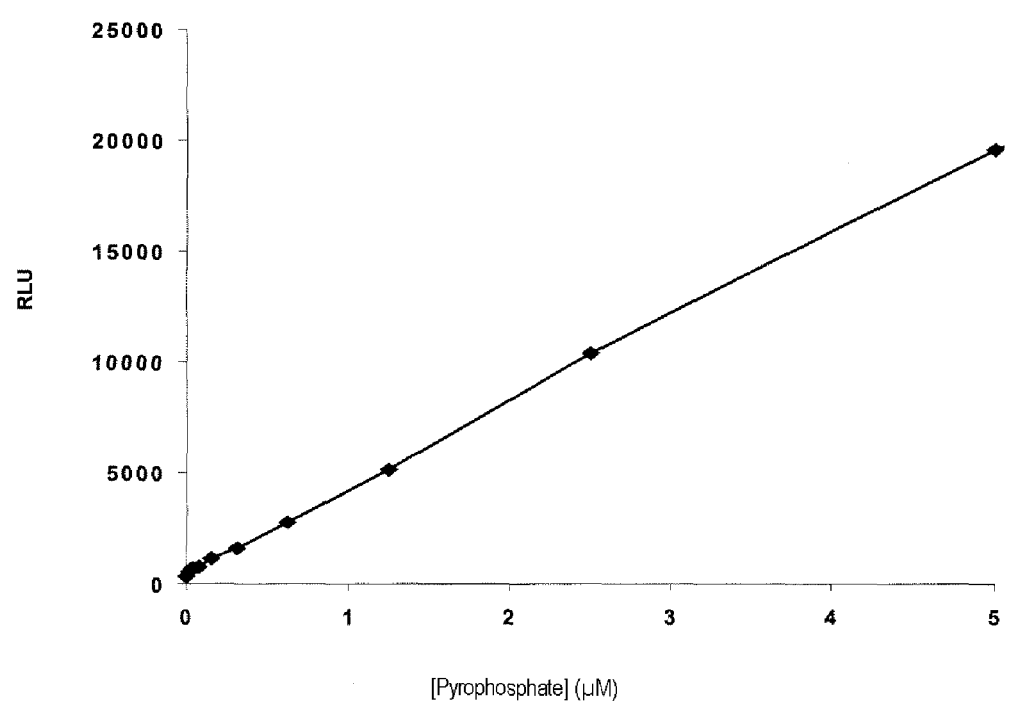

The novel methods are distinguished by high sensitivity and low susceptibility to interference, can easily be automated and miniaturized and are additionally suitable for carrying out continuous measurements. The methods can be employed particularly advantageously in the area of medical diagnosis and biomedical research, including pharmaceutical active ingredient research.

11 Claims, 4 Drawing Sheets

METHOD FOR DETECTING PYROPHOSPHATE BY MEANS OF BIOLUMINESCENCE DETECTION

RELATED APPLICATIONS/PATENTS AND INCORPORATION BY REFERENCE

This application is a National Stage Application filed under 35 U.S.C. §371 based on International Application No. PCT/EP2007/009625, filed Nov. 7, 2007, which claims priority to German Patent Application Number 102006054562.1, filed Nov. 20, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The invention relates to methods for detecting pyrophosphate by means of bioluminescence detection. In addition, methods for measuring chemical, especially enzyme-catalyzed, reactions in which pyrophosphate is formed or consumed are described. Such reactions are catalyzed for example by guanylyl cyclases, adenylyl cyclases, DNA polymerases or RNA polymerases.

The novel methods are distinguished by high sensitivity and low susceptibility to interference, can easily be automated and miniaturized and are additionally suitable for carrying out continuous measurements. The methods can be employed particularly advantageously in the area of medical diagnosis and biomedical research, including pharmaceutical active ingredient research.

Pyrophosphate (diphosphate(V), PPi) is a central metabolite of cellular metabolism which is formed or consumed in numerous enzymatic reactions; thus, for example, central metabolic reactions such as the synthesis of polysaccharides, proteins and nucleic acids take place with formation of pyrophosphate. Pyrophosphate moreover occurs in the inanimate environment and is formed or consumed in various industrial reactions.

Methods for the detection and quantification of pyrophosphate can therefore be employed in various areas; of special interest is the use in the area of medical diagnosis, of biomedical research, in particular of active ingredient research and pharmaceutical research, and in the area of environmental and food analyses. Besides the analysis of pyrophosphate contents, it is particularly important in this connection to measure chemical reactions in which pyrophosphate is formed or consumed, and to determine enzyme activities which catalyze such reactions.

In the area of medical diagnosis, the use of methods for detecting pyrophosphate is appropriate whenever the pyrophosphate content of the test sample can be an indicator of a pathological change. Samples of particular interest may be of body fluids or tissue preparations, for example samples of blood, serum, urine, spinal fluid, synovial fluid or preparations thereof. Methods for analyzing such test samples ought to be distinguished by maximal sensitivity and low susceptibility to interference, especially from typical sample constituents such as, for example, phosphate or ATP. In addition, it is desirable for efficient and cost-effective performance of the analyses that the methods can be easily automated and miniaturized.

In the area of biomedical research, especially of active pharmaceutical ingredient research, in order to find new candidate active ingredients regularly large substance libraries with, in some cases, more than one million substances are screened with the aid of automated methods (high throughput screening); the screening in this case is typically aimed at identifying modulators of a biological activity, for example an enzyme activity, which might be the target of a medical therapy. Enzymes which catalyze pyrophosphate-forming or -consuming reactions and might be the target of a medical therapy are for example guanylyl cyclases, adenylyl cyclases, DNA polymerases and RNA polymerases, and squalene synthase. Methods for measuring such enzyme activities in pharmaceutical high throughput screening ought to be easily automatable and, to limit the costs for reagents and test substances, also miniaturizable. In addition, it is desirable for the sensitivity to be as high as possible for detecting even low enzyme activities, and for the susceptibility to interference to be as low as possible to achieve a high data quality.

For further enzyme-kinetic characterization of the modulators, including determination of the mechanism of inhibition, of the rate of formation and dissociation of the enzyme-modulator complex or of the energy consumptions associated with the formation and dissociation of the enzyme-modulator complex, typically the course of the investigated enzyme reactions are recorded and analyzed. Suitable methods ought therefore to depict the course of the reaction with maximal time resolution, ideally continuously.

A continuous measurement of the pyrophosphate concentration may also be desirable in applications in the area of genome analysis and gene expression analysis, for example in nucleic acid sequencing (pyrosequencing) or the measurement of nucleic acid amplifications by polymerase chain reaction (quantitative PCR). Methods suitable in these connections are additionally distinguished by minimal susceptibility to interference from phosphate and ATP.

Bioluminescence is a phenomenon which is widespread in nature but is also used technically and refers to the emission of light in the course of an enzyme-catalyzed chemical reaction; bioluminogenic reactions are catalyzed for example by luciferases or photoproteins. The oxidative decarboxylation, catalyzed by *Photinus pyralis* luciferase, of D-luciferin to oxyluciferin in the presence of adenosine triphosphate (ATP), $Mg^{2+}$ and oxygen ($O_2$) has long been known. Investigations to characterize this reaction and the reaction mechanism are set forth relatively precisely for example in McElroy, Proc. Natl. Acad. Sci. USA 33 (1947) 342-345, McElroy, J. Biol. Chem. 191 (1951) 547-557, McElroy et al., Arch. Biochem. Biophys. 46 (1953) 399-416, Green & McElroy, Biochim Biophys. Acta 20 (1956) 170-176, Bitler & McElroy, Arch. Biochem. Biophys. 72 (1957) 358-368, Rhodes et al., J. Biol. Chem. 233 (1958) 1528-1537, White et al., J. Am. Chem. Soc. 85 (1963) 337-343, Denburg et al., Arch. Biochem. Biophys. 134 (1969) 381-394, Lee et al., Arch. Biochem. Biophys. 141 (1970) 38-52, Denburg & McElroy, Arch. Biochem. Biophys. 141 (1970) 668-675, Lundin, (1993) in: Biolum. Chemilum.: Status Report (Ed. Szalay, Kricka), 291-295, Fontes et al., Biochem. Biophys. Res. Comun. 237 (1997) 445-450, Fontes et al., FEBS Lett. 438 (1998) 190-194, Sillero et al., Pharmacol. Therap. 87 (2000) 91-102, WO 9640988 and Eriksson et al., Anal. Biochem. 293 (2001) 67-70; in this connection, both activating and inhibiting effects of pyrophosphate are described. The luminescent light emitted during the reaction can be measured very sensitively and thus the course of the reaction can be followed accurately. The reaction catalyzed by *Photinus pyralis* luciferase is employed normally for detecting ATP, but also for measuring enzyme reactions in which ATP is formed or consumed (Lundin (1982), in Luminescent Assays: Perspectives in Endocrinology and Clin.

Chem. (Ed. Serio, Pazzagli) 29-45). The gene of the *Photinus pyralis* luciferase is moreover frequently used as reporter gene in cellular assay systems (Gould et al., Anal. Biochem. 175 (1988) 5-13).

It is known that all beetle luciferases (luciferases isolated from the superfamilies Elateroidea and Cantharoidea) catalyze a bioluminogenic reaction which consumes the same substrates adenosine triphosphate (ATP), luciferin and molecular oxygen. It is to be assumed that all beetle luciferases use the same reaction mechanism (U.S. Pat. No. 6,387,675 B1).

Various methods for detecting pyrophosphate are known in the prior art.

Flynn et al., J. Biol. Chem. 211 (1954) 791-796, Grindey et al., Anal. Biochem. 33 (1970) 114-119, Putnins et al., Anal. Biochem. 68 (1975) 185-195, Heinonen et al., Anal. Biochem. 117 (1981) 293-300, and Mansurova et al., Anal. Biochem. 176 (1991) 390-94 describe direct chemical detection methods for pyrophosphate. In the methods described, the pyrophosphate-containing test sample is mixed with an acidic molybdate solution and a reducing thiol reagent (cysteine, bisulfide/thioglycerol or mercaptoethanol), and the resulting blue complexes are quantified by UV spectrometry. One problem is the susceptibility of these detection methods to interference, especially from phosphate. In addition, the slow complex formation (with cysteine >10-15 min) is disadvantageous for efficient automated performance.

Heinonen et al., Anal. Biochem. 59 (1974) 366-374, and Russel et al., J. Clin. Invest. 50 (1971) 961-969, describe radioactive detection methods which include a plurality of elaborate steps and can therefore be automated only with difficulty. In addition, these methods are unsuitable for continuous measurements to determine the time course of a pyrophosphate sample concentration.

In addition, pyrophosphate detections with coupled enzyme reactions are known in the prior art; in these methods, pyrophosphate is converted enzymatically and detected as reaction product by one or by a plurality of coupled enzyme reactions.

A method of this type is described for example by Johnson et al., Anal. Biochem. 26 (1968) 137-145; in this case, pyrophosphate is converted with UDP-glucose with catalysis by glucose pyrophosphatase into UTP and glucose 1-P; the glucose 1-P formed isomerizes with catalysis by phosphoglucomutase to glucose 6-P which reacts to give gluconolactone 6-P catalyzed by glucose-6-P dehydrogenase with consumption of NADP. The NADPH formed in this case is quantified by UV absorption measurement and used to determine the pyrophosphate content in the test sample. Further detection methods for pyrophosphate with coupled enzyme reactions are described for example by Cartier et al., Anal. Biochem. 61 (1974) 416-428, Cheung et al., Anal. Biochem. 83 (1977) 61-63, Reeves et al., Anal. Biochem. 28 (1969) 282-287, Arakawa et al., Anal. Biochem. 333 (2004) 296-302, Guillory et al., Anal. Biochem. 39 (1971) 170-180, Cook et al., Anal. Biochem. 91 (1978) 557-565, Jansson et al., Anal. Biochem. 304 (2002) 135-137, Tagiri-Endo, Anal. Biochem. 315 (2003) 170-174, Drake et al., Anal. Biochem. 94 (1979) 117-120, Nyren et al., Anal. Biochem. 151 (1985) 504-509, and Barshop et al., Anal. Biochem. 197 (1991) 266-72.

These methods have the disadvantage that the enzymes and other reagents required are often difficult to obtain or can be purchased only at high cost. In addition, these methods are fundamentally susceptible to interference from substances which modulate the enzyme activity of the coupling enzymes used; this considerably limits their employability especially in the area of medical diagnosis and biomedical research, for example pharmaceutical high throughput screening.

Also known in the prior art is the use of phosphate detections for indirect detection of pyrophosphate; in these cases, pyrophosphate is initially cleaved enzymatically or chemically, and the resulting phosphate is detected and quantified. Methods of this type are described for example in Fiske et al., J. Biol. Chem. 66 (1925) 375, Silcox et al., J. Clin. Invest. 52 (1973) 1863-1870, Gibson et al., Anal. Biochem. 254 (1997) 18-22, Cogan et al., Anal. Biochem. 271 (1999) 29-35, Upson et al., Anal. Biochem. 243 (1996) 41-45, WO 0042214 and Baykov et al., Anal. Biochem. 119 (1982) 211-213. These methods are typically unsuitable for continuous measurements and fundamentally susceptible to interference from phosphate.

Fabbrizzi et al., Angew. Chem. Int. Ed. 41 (2002) 3811-3814, describe a detection method with fluorescence detection which is based on the pyrophosphate-mediated displacement of an indicator molecule from a selective receptor molecule. The method has only low sensitivity with a limit of detection in the micromolar concentration range.

The method of Eriksson et al., Anal. Biochem. 293 (2001) 67-70, likewise has low sensitivity, with a limit of detection in the medium micromolar concentration range. In this case, a luciferase-catalyzed luminescence reaction with both luciferin enantiomers, D-luciferin and L-luciferin, and a small amount of ATP is used. Detection takes place via an inhibiting effect of pyrophosphate on the luminescence reaction and the decrease, associated therewith, in the emission of light. Eriksson et al. additionally describe the use of this detection method for determining the enzyme activity of pyrophosphatase; in this case, introduced pyrophosphate is broken down by pyrophosphatase, and the increase in the emission of light is measured.

DE 19602662 describes a method for detecting pyrophosphate in which the pyrophosphate test sample is added to a preincubated mixture of luciferase, L-luciferin, ATP and pyrophosphatase, and thereby generates a light flash; the light flash is recorded and used to determine the pyrophosphate concentration. Detection of pyrophosphate in concentrations of from 10 µM to 100 µM is described. The method is unsuitable for continuous measurements.

DE 10250491 describes a detection method for pyrophosphate using a polymerase with pyrophosphorolysis activity and a specifically labeled oligonucleotide indicator substrate; added pyrophosphate leads to the pyrophosphorolytic breakdown of the indicator substrate with liberation of a labeled mononucleotide which is finally quantified. A disadvantage is the susceptibility of this method to interference from nucleic acid-intercalating substances, which considerably restricts the use in the area of active pharmaceutical ingredient research, including pharmaceutical high throughput screening.

WO 0036151 relates to a method for detecting the enzymatic elimination of pyrophosphate from nucleotide triphosphates. The substrates used are nucleotide triphosphates which are modified both with a fluorophor and with a fluorescence quencher; the enzymatic cleavage of the substrate liberates fluorophor-labeled pyrophosphate which is detected and finally quantified. Owing to the labels introduced, the described substrates can be employed to only a limited extent instead of the natural nucleotide triphosphates, depending on the cleaving enzyme.

Methods for measuring the enzyme activity of guanylyl cyclases are also known in the prior art.

Guanlylyl cyclases (E.C. 4.6.1.2) catalyze the conversion of guanosine triphosphate (GTP) into cyclic 3'-5'-guanosine monophosphate (cGMP) and pyrophosphate.

Domino et al., Methods in Enzymology 105 (1991) 345-355, describe a method using radiolabeled GTP which is converted into cGMP during the reaction catalyzed by guanylyl cyclase. The cGMP formed is separated from unreacted GTP, quantified by radioactivity measurement and used to calculate the enzyme activity. The method includes a plurality of elaborate steps and can therefore be automated only with difficulty. In addition, the method is unsuitable for carrying out continuous measurements.

In addition, various immunoassays using cGMP-specific antibodies are known (product description for CatchPoint cGMP Fluorescent Assay Kit, Molecular Devices; product description for HTRF cGMP Assay, Cisbio international, product description for cGMP EIA Kit, Alexis Biochemicals, product description for HitHunter cGMP Assay, DiscoverRx). In these cases, the cGMP formed is detected indirectly by displacement and quantification of a probe bound to the antibody (competitive immunoassay). The disadvantages of these methods are the high reagent costs or preparative efforts to provide the necessary antibodies, which considerably restricts the use in high throughput experiments such as, for example, pharmaceutical high throughput screening. The methods are moreover unsuitable for carrying out continuous measurements. In addition, several methods include elaborate steps, especially washing procedures, which considerably impede efficient automation.

US 20040229251 describes a method in which fluorophor-labeled GTP, specifically BODIPY-labeled GTP, is used as surrogate substrate. The described method has the intrinsic disadvantage that the reaction is not carried out with the natural substrate, possibly leading to systematic artifacts. The high reagent costs or preparative efforts for providing the described surrogate substrate additionally restrict the possibilities of use in the area of high throughput experiments, including pharmaceutical high throughput screening.

Methods for measuring the enzyme activity of squalene synthase are also known in the prior art.

Squalene synthase (E.C. 2.5.1.21) is a bifunctional enzyme which in a first catalytic step mediates the condensation of two molecules of farnesyl pyrophosphate (FPP) to give presqualene pyrophosphate. In a second catalytic step, presqualene pyrophosphate is converted into squalene. One molecule of pyrophosphate is formed, and two molecules of NADPH are consumed, in each of the two steps.

Several radioactive methods are known in the prior art (A. Qureshi et al., J. Biol. Chem. 248 (1973) 1848, Ishihara et al., Bioorg. Med. Chem. 11 (2003) 2403, H. Hiyoshi et al., J. Lip. Res. 41 (2000) 1136). In these methods, radiolabeled FPP is employed as substrate, and the squalene formed during their reaction is taken up in organic solvents, separated out by chromatography and finally quantified. These methods are extremely experimentally elaborate and can be automated only with difficulty. In addition, these methods do not permit continuous measurements.

US 20030157583 describes a method based on measurement of the NADPH consumption which, as already described above, is coupled to the progress of the reaction. This method has only limited sensitivity and is unsuitable for measuring low enzyme activities.

The invention is now based on the object of overcoming the stated disadvantages and restrictions of the prior art and providing a method for detecting pyrophosphate which is distinguished by high sensitivity and low susceptibility to interference, can easily be automated and miniaturized and is additionally suitable for carrying out continuous measurements.

The object is achieved according to the invention by methods for detecting pyrophosphate with bioluminescence detection.

The invention relates to methods for detecting pyrophosphate which include the following stages:
(a) providing a composition comprising dehydroluciferin, luciferin, ATP and a luciferase which can be activated by pyrophosphate, e.g. a luciferase from *Photinus pyralis;*
(b) contacting the composition with the test sample; and
(c) measuring luminescence.

The composition used in stage (a) of the method of the invention is in a preferred embodiment an aqueous solution comprising dehydroluciferin, luciferin, ATP and *Photinus pyralis* luciferase and can be obtained by combining aqueous solutions of the individual components. Luciferin, ATP and *Photinus pyralis* luciferase are commercially available, with preference for products of high purity and, in the case of *Photinus pyralis* luciferase, also of high specific enzyme activity. Dehydroluciferin can easily be obtained from commercially available luciferin by a method described in the prior art (Bitler & McElroy, Arch. Biochem. Biophys. 72 (1957) 358). Aqueous solutions of the individual components can be prepared with the required concentrations without difficulty.

The invention relates to the use of non-recombinant or recombinant luciferases and variants derived or mutated therefrom, characterized in that they catalyze bioluminogenic biochemical reactions.

The invention relates to the use of non-recombinant or recombinant luciferases whose bioluminogenic biochemical reaction can be activated by pyrophosphate, and variants derived or mutated therefrom. Activation of a bioluminogenic biochemical reaction of a luciferase can take place by abolishing a product inhibition or by direct, for example allosteric, enzyme activation or by other mechanisms.

The invention relates to the use of luciferases and recombinant luciferases, originally isolated from insects of the superfamilies Elateroidea and Cantharoidea, characterized in that they catalyze ATP- and luciferin-consuming bioluminogenic biochemical reactions, for example selected, but not restricted by, from the insects *Photinus pyralis, Pyrophorus plagiophthalamus, Luciola cruciata, Luciola lateralis* or *Luciola mingrelica* (U.S. Pat. No. 6,387,675 B1, Wood et al., J. Biolum. Chemilum. 4 (1989) 289-301, Wood et al., J. Biolum. Chemilum. 4 (1989) 31-39, Tatsumi et al., Biochim Biophys. Acta 1131 (1992) 161-165). The invention particularly preferably relates to the use of the luciferase from *Photinus pyralis.*

The invention relates to the use of luciferase mutants which are distinguished by having altered spectral bioluminescence properties, for example selected, but not restricted, by substitutions which correspond to the amino acid positions 215, 224, 232, 236, 237, 242, 244, 245, 248, 282, 283 or 348 of the luciferase LucPplGR from *Pyrophorus plagiophthalamus* (U.S. Pat. No. 6,387,675 B1).

The invention further relates to the use of luciferase mutants which are distinguished by having altered thermal stability, for example selected, but not restricted, by substitutions of corresponds to amino acid position 217 of the luciferases from *Luciola cruciata* or *Luciola lateralis* by a hydrophobic amino acid (U.S. Pat. No. 5,229,285).

The invention further relates to the use of luciferase mutants which are distinguished by having altered thermal stability, for example selected, but not restricted, by substitutions of corresponds to amino acid position 286 (serine by asparagine), amino acid position 326 (glycine by serine), amino acid position 433 (histidine by tyrosine) or amino acid position 452 (proline by serine) of the luciferase from *Luciola cruciata* (U.S. Pat. No. 5,219,737).

The preferred embodiment of the composition as aqueous solution comprising the listed components comprises dehydroluciferin in a preferred concentration range from 5 µM to 250 µM, with the range from 10 µM to 100 µM being more preferred and the range from 20 µM to 40 µM being most preferred, luciferin in a preferred concentration range from 10 µM to 500 µM, with the range from 30 µM to 300 µM being more preferred and the range from 70 µM to 200 µM being most preferred, ATP in a preferred concentration range from 10 µM to 500 µM, with the range from 30 µM to 300 µM being more preferred and the range from 70 µM to 200 µM being most preferred, and

*Photinus pyralis* luciferase in a preferred concentration range from 0.1 nM to 10 nM, with the range from 0.3 nM to 3 nM being more preferred and the range from 0.5 nM to 2 nM being most preferred.

The composition used in stage (a) of the method of the invention may comprise additional components, for example buffer substances, monovalent and divalent salts, reducing agents, especially those containing free mercapto groups, proteins, synthetic polymers and detergents.

Examples of buffer substances are HEPES, TEA, tris, tricine, MES and MOPS, with preference for TEA and tris. Buffer substances are preferably present in concentrations from 10 mM to 100 mM. The pH is preferably in the range from 7.0 to 8.0, even more preferably in the range from 7.3 to 7.7.

Examples of monovalent salts are NaCl, KCl, NH4Cl, Na acetate, K acetate, NH4 acetate, with preference for NaCl and KCl. Monovalent salts are preferably present in concentrations from 0 mM to 200 mM.

Examples of divalent salts are MgCl2, MgSO4, Mg acetates, MnCL2 and CaCl2, with preference for MgCl2. Divalent salts are preferably present in concentrations from 1 mM to 10 mM.

Examples of reducing agents, especially those containing free mercapto groups, are mercapto ethanol, DTE, DTT and glutathione, with preference for DTT. Reducing agents are preferably present in concentrations from 0.2 mM to 20 mM.

Examples of additional proteins or synthetic polymers are BSA, HSA, hemoglobin, casein and PEG, with preference for BSA. Additional proteins or synthetic polymers are preferably present in concentrations from 0.01% to 1% (weight per volume).

Examples of detergents are Brij, Tween, CHAPS, TRITON and NP-40, with preference for Brij and CHAPS. Detergents are preferably present in concentrations from 0.001% to 0.01% (weight per volume).

A particularly preferred embodiment of the composition comprises as additional components 50 mM TEA (pH=7.5), 2 mM MgCl2, 0.4 mM DTT, 0.1% (w/v) BSA (fraction V), and 0.005% (w/v) Brij-35.

As already pointed out above, the preferred embodiment of the composition as aqueous solution comprising dehydroluciferin, luciferin, ATP and *Photinus pyralis* luciferase can be obtained by combining aqueous solutions of the individual components; this preferably entails initially combining aqueous solutions of *Photinus pyralis* luciferase, dehydroluciferin and ATP and finally adding luciferin, preferably in aqueous solution. The initially combined solutions of *Photinus pyralis* luciferase, dehydroluciferin and ATP can be incubated before the addition of luciferin, with an incubation time in the range from 1 min to 15 min and an incubation temperature in the range from 15° C. to 30° C. being preferred.

It is particularly preferred to prepare a composition preferably used in stage (a) of the method of the invention by the following method including the stages:

(a) combining aqueous solutions of *Photinus pyralis* luciferase, dehydroluciferin and ATP, which comprise in each case as additional components 50 mM TEA (pH=7.5), 2 mM MgCl$_2$, 0.4 mM DTT, 0.1% (w/v) BSA (fraction V), and 0.005% (w/v) Brij-35, (b) incubating the combination from (a) at a temperature of 20° C. to 25° C. for 5 min to 10 min;

(c) supplementing the incubated combination from (b) with an aqueous solution of luciferin, which comprises as additional components 50 mM TEA (pH=7.5), 2 mM MgCl$_2$, 0.4 mM DTT, 0.1% (w/v) BSA (fraction V), and 0.005% (w/v) Brij-35.

A composition used in stage (a) of the method of the invention and comprising dehydroluciferin, luciferin, ATP and *Photinus pyralis* luciferase, plus additional components, in aqueous solution can be stored. The storage stability of the composition depends inter alia on the selection and concentration of the additional components and on the storage conditions. A storage stability of several days to weeks is typically achieved. Preferred storage temperatures are in the range from 2° C. to 10° C. The composition can also be stored in the frozen state, preferably below minus 70° C.; in this case, the composition must be frozen as quickly as possible, preferably shock-frozen.

A composition used in stage (a) of the method of the invention and comprising in aqueous solution dehydroluciferin, luciferin, ATP and *Photinus pyralis* luciferase, and as additional components 50 mM TEA (pH=7.5), 2 mM MgCl$_2$, 0.4 mM DTT, 0.1% (w/v) BSA (fraction V), and 0.005% (w/v) Brij-35 can typically be stored for several days, but at least 24 hours, at 4° C. to 10° C.

The test sample is preferably an essentially aqueous sample and it may be a sample which is essentially already aqueous as such or the product of a previously carried out sample preparation, for example an extraction.

The test sample may originate from a natural source including the animate and inanimate environment. Examples of test samples from the inanimate environment are water samples or extracts from soil, sand or stone. Examples of test samples from the animate environment are samples from animal or plant organisms. Samples of particular interest are those from the human body, possibilities being tissue samples or samples of body fluids or preparations thereof. Examples of such body fluids are blood, serum, urine, spinal fluid, synovial fluid or preparations thereof.

The test sample may additionally also be a chemical reaction in which pyrophosphate is produced or consumed. Of particular interest in this connection are enzyme-catalyzed chemical reactions (enzyme reactions) in which pyrophosphate is produced or consumed. Such reactions are catalyzed for example by guanylyl cyclases, adenylyl cyclases, DNA polymerases or RNA polymerases, squalene synthase or pyrophosphatase.

In a preferred embodiment, the method of the invention is carried out in homogeneous phase. In this embodiment, the method of the invention can be particularly easily automated and miniaturized. For this purpose, in stage (b) of the method, the composition as aqueous solution comprising dehydroluciferin, luciferin, ATP and *Photinus pyralis* luciferase is combined with the essentially aqueous test sample. The resulting test volume is preferably below 1000 µl, more preferably below 100 µl, most preferably below 10 µl.

Combining the composition and test sample can be carried out with commercially available devices for manipulating fluids (liquid handling systems). Examples of suitable devices are pipetting devices, including micropipettes and parallel pipettors, dispensing devices, including piezo effect-based systems, bubble jet systems, and dispensing instruments with valve control, and transfer devices, including pin tool-based systems.

The method of the invention can be carried out in commercially available reaction vessels, preferably microplates with 96, 384 or 1536 wells. Microplates with 1536 wells are particularly preferred. Also suitable as reaction chambers are capillaries or capillary systems, and cavities of porous materials, including polymer gels and porous microspheres (beads). It can also conceivably be carried out on microsupports (chips) or in liquid films on microscope slides or on microspheres (beads). The method could also be carried out as process or part of the process of a lab on the chip concept.

In a further embodiment, the method of the invention can also be carried out in a heterogeneous phase assemblage. In this case, at least one component of the test sample or the composition is present in a further phase.

In a preferred embodiment, *Photinus pyralis* luciferase is immobilized on a suitable solid support and activated by contacting with an aqueous composition comprising dehydroluciferin, luciferin and ATP. The essentially aqueous test sample is then contacted with the immobilized luciferase, preferably in the mixture with the activating composition, and the emitted luminescence is measured. The luciferase can be immobilized, depending on a device, for example on the surface of capillaries, capillary systems, microsupports (chips) or microspheres (beads).

The luminescence to be measured in stage (c) of the method of the invention correlates with the pyrophosphate concentration in the test sample (compare Example 1), with a higher pyrophosphate concentration leading to a stronger luminescence signal. In the concentration range below 20 µM pyrophosphate, typically a linear correlation is observed between luminescence signal and pyrophosphate concentration (compare Example 1). The method of the invention is therefore particularly suitable for detecting pyrophosphate in concentrations below 20 µM. The preferred range is a pyrophosphate concentration in the test sample of from 20 nM to 20 µM, the more preferred range is from 50 nM to 10 µM, and the most preferred range is from 100 nM to 1 µM.

For a quantitative determination of the pyrophosphate concentration in the test sample, additional reference samples of known pyrophosphate concentration are treated and measured in the same way as the test sample; a correlation of luminescence signal and pyrophosphate concentration under the given experimental conditions is derived from this additional investigation, it being possible for the measured data for example to be interpolated graphically or approximated by electronic processing. A pyrophosphate concentration can be attributed directly to the luminescence value measured for the test sample from the derived correlation.

The measurement of luminescence in stage (c) of the method of the invention can be carried out with commercially available luminometers; however, depending on the embodiment of the method, especially of the reaction vessel, special reading instruments may be necessary.

The test mixture is preferably measured directly in the reaction vessel; in this case, measurements directly in microplates having 96, 384 or 1536 wells are preferred. Depending on the embodiment of the method, however, it may also be advantageous for the test mixture to be transferred wholly or partly into a further vessel suitable for the measurement and only then be measured.

If the pyrophosphate concentration in the test sample is to be determined at various times, the measurement of the luminescence in stage (c) of the method of the invention can be carried of repeatedly, with the test mixture being measured directly in the reaction vessel, or aliquots can be transferred into further vessels suitable for the measurement, and measured, at the desired times. In both cases, the detection reaction should if possible not interfere with the processes in the test sample which determine or influence the pyrophosphate concentration. In an alternative procedure, it is also possible for aliquots to be taken from the test sample directly at the desired times, and for these aliquots to be contacted with the composition and then measured.

After the test sample has been contacted in stage (b) of the method of the invention with the composition, the resulting luminescence signal which is to be measured in stage (c) develops rapidly, typically within seconds. The signal ordinarily has an intensity which can be determined reliably with commercially available luminometers within short integration times, typically within seconds.

The method of the invention therefore makes it possible to determine pyrophosphate concentrations particularly quickly and in timely fashion. Because of the quickness, the method is preferably suitable also for time-resolved determination of the pyrophosphate concentration in a test sample, it being possible to proceed in the manner already detailed above.

Time-resolved determinations of pyrophosphate concentrations are of interest particularly when the test sample comprises chemical, including enzyme-catalyzed chemical reactions in which pyrophosphate is formed or consumed. It is possible on the basis of the time course of the pyrophosphate concentration to calculate the rate of conversion in the investigated reaction and also the activity of the enzyme employed where appropriate in a known manner.

The invention further relates to methods for detecting pyrophosphate which include the following stages:
(a) contacting the components of a composition comprising dehydroluciferin, luciferin, ATP and a luciferase which can be activated by pyrophosphate, e.g. a luciferase from *Photinus pyralis*; with the test sample
(b) measuring luminescence.

Stage (a) of the method should preferably be carried out rapidly, meaning within minutes, depending on the sequence in which the components of the composition and the test sample are combined. The luminescence signal to be measured in stage (b) of the method might, depending on the sequence in which the components of the composition and the test sample are combined, and depending on the additional components, initially develop over a short time interval and only then stabilize; in these cases, the stabilized luminescence intensity is to be used for determining the pyrophosphate concentration.

The composition and the included individual components are preferably configured and combined as aqueous solutions; the solutions may, as already explained above, comprise additional components.

The combining of the aqueous components, and the contacting with the test sample, as well as the subsequent measuring of the luminescence can be carried out in the manner already explained above.

In a preferred embodiment of the method, firstly a combination include dehydroluciferin, ATP and *Photinus pyralis* luciferase is provided in stage (a); the combination is then contacted with the test sample, and finally luciferin is added.

The combination including dehydroluciferin, ATP and *Photinus pyralis* luciferase can be stored. The storage stability of the combination depends inter alia on the selection and concentration of the additional components and on the storage conditions.

The invention additionally relates to methods for measuring the time course of a pyrophosphate-forming or -consuming enzyme reaction, which include the following stages:
(a) providing a composition including dehydroluciferin, luciferin, ATP and a luciferase which can be activated by pyrophosphate, e.g. a luciferase from *Photinus pyralis;*
(b) contacting the composition with the pyrophosphate-forming or -consuming enzyme reaction; and
(c) continuously measuring luminescence.

The composition including dehydroluciferin, luciferin, ATP and *Photinus pyralis* luciferase is, as already explained above, preferably configured as aqueous solution and may comprise additional components.

The provision of the composition by combining the preferably aqueous components, and the contacting with the test sample can likewise be carried out in the manner explained hereinbefore.

For continuous measurement of luminescence in stage (c) of the method, individual measurements with short integration periods are carried out at short intervals. It is possible with commercially available instruments to measure, reliably and at short intervals, meaning at an interval of less than one second, typical luminescence signals with integration periods in the region of a few seconds, and in some cases of less than one second.

The method of the invention makes it possible, as already stated above, to determine the respective pyrophosphate concentration particularly quickly and in timely fashion. It is possible with the aid of the described continuous luminescence measurement to determine and follow the course of the pyrophosphate concentration with high time resolution. In a pyrophosphate-forming or -consuming reaction, the time course of the pyrophosphate concentration can be used as indicator of the course of the reaction, and the reaction conversion achieved in each case, and the respective reaction rate, including the respective activity of the enzyme employed, can be calculated in a known manner.

The start and duration of the continuous luminescence measurement in stage (c) of the method may be varied depending on the experimental objective. In a preferred embodiment, the enzyme reaction is initiated immediately before starting the luminescence measurement. It is possible in this way to achieve the determination of initial reaction rates which is desired in many enzyme-kinetic investigations.

The invention additionally relates to methods for measuring the time course of a pyrophosphate-forming or -consuming enzyme reaction, which include the following stages:
(a) contacting one or more components of the pyrophosphate-forming or -consuming enzyme reaction with a composition including dehydroluciferin, luciferin, ATP and a luciferase which can be activated by pyrophosphate, e.g. a luciferase from *Photinus pyralis;*
(b) contacting the combination of (a) with the remaining components of the pyrophosphate-forming or -consuming enzyme reaction; and
(c) continuously measuring luminescence.

The composition comprising dehydroluciferin, luciferin, ATP and *Photinus pyralis* luciferase is, as already explained above, preferably configured as aqueous solution and may comprise additional components.

The provision of the composition by combining the preferably aqueous components, the contacting with the components of the pyrophosphate-forming or -consuming enzyme reaction and the continuous measurement of luminescence can likewise be carried out in the manner explained hereinbefore.

In a preferred embodiment, the combination from stage (a) of the method is incubated before starting stage (b); the incubation preferably takes place at the intended reaction temperature, for example 37° C., and over a period sufficient to bring at least the total volume of the combination to the intended reaction temperature. It is additionally preferred for stage (a) to be configured in such a way that only one remaining component of the pyrophosphate-forming or -consuming enzyme reaction is contacted with the combination from stage (a) in stage (b) and thus the reaction is initiated (compare Example 2: measurement of an enzyme reaction catalyzed by soluble vascular guanylate cyclase). In this case, the one remaining component is preferably added with the aid of a dispensing device directly in the luminometer, so that the continuous measurement of luminescence can be started directly, meaning with a time interval typically of less than one second. Alternatively, the measurement can also be started even before adding the one remaining component, in which case the appropriate sections of the measurement are used to determine the initial reaction rate or the enzyme activity.

The invention additionally relates to methods for measuring the time course of a pyrophosphate-forming or -consuming enzyme reaction, which include the following stages:
(a) contacting the components of the pyrophosphate-forming or -consuming enzyme reaction with the components of a composition including dehydroluciferin, luciferin, ATP and a luciferase which can be activated by pyrophosphate, e.g. a luciferase from *Photinus pyralis;*
(b) continuously measuring luminescence.

The composition including dehydroluciferin, luciferin, ATP and *Photinus pyralis* luciferase is, as already explained above, preferably configured as aqueous solution and may comprise additional components. The contacting of the components of the composition with the components of the pyrophosphate-forming or -consuming enzyme reaction and the continuous measurement of luminescence can likewise be carried out in the manner explained hereinbefore.

Stage (a) of the method should preferably be carried out rapidly, meaning within minutes, depending on the sequence in which the components of the composition and the components of the pyrophosphate-forming or -consuming enzyme reaction are combined. The luminescence signal to be measured in stage (b) of the method might, depending on the sequence in which the components of the composition and the components of the pyrophosphate-forming or -consuming enzyme reaction are combined, and depending on the additional components, initially develop over a short time interval and only then stabilize; suitable later sections of the continuous luminescence measurement are to be used for determining the reaction rate or the enzyme activity in these cases.

The methods of the invention can be employed advantageously in various areas; use of particular interest is in the area of medical diagnosis, of biomedical research, in particular of active ingredient research and pharmaceutical research, and in the area of environmental and food analyses. It is moreover possible for the use of the methods of the invention to be directed not only at the determination of pyrophosphate concentrations but also at the measurement of chemical reaction conversions and enzyme activities.

The methods of the invention can, as already explained above, be carried out in homogeneous phase and in a few simple processing stages; they are therefore excellently suited for automation and miniaturization.

In the area of medical diagnosis, the use of methods of the invention is appropriate whenever the pyrophosphate content of the test sample can be an indicator of a pathological change. Samples of particular interest may be of body fluids or tissue preparations, for example samples of blood, serum, urine, spinal fluid, synovial fluid or preparations thereof. The methods of the invention are excellently suited, because of the high sensitivity and low susceptibility to interference, in particular from typical sample constituents such as phosphate or ATP, for analyzing such test samples. In addition, the easy automatability and miniaturizability of the methods of the invention make it possible to carry out the analyses particularly efficiently and cost-effectively.

Automated use of the methods of the invention may additionally be important in the area of biomedical research, especially of active pharmaceutical ingredient research; in this, regularly large substance libraries with, in some cases, more than one million substances are screened with the aid of automatic methods (high throughput screening) in order to find new candidate active ingredients; besides the easy automatability of the methods, in particular the miniaturizability, the high sensitivity and the low susceptibility to interference are advantageous for this application. Miniaturization of the test formats and the high sensitivity reduce the efforts for preparing or acquiring reagents and the consumption of test substances. Low susceptibility to interference normally leads to high data quality and good reproducibility of the test results.

Pharmaceutical high throughput screening is typically directed at identifying modulators of a biological activity, for example an enzyme activity, which may be the target of a medical therapy. The methods of the invention are excellently suited for such a use in pharmaceutical high throughput screening, specifically for finding modulators of enzymes which catalyze pyrophosphate-forming or -consuming reactions; of particular interest in this connection are for example modulators of the enzyme activity of guanylyl cyclases, adenylyl cyclases, DNA polymerases or RNA polymerases or of squalene synthase. For this purpose, the activity of the relevant enzyme is determined by one of the methods of the invention described above in the presence of one or more suitable concentration of the test substance and compared with the activity of the enzyme in the absence of the test substance, and the modulating properties of the test substance are derived therefrom in a known manner. Normally derived properties of a test substance are the activating or inhibiting effect on the investigated enzyme activity (compare Examples 3 and 5).

In addition, the methods of the invention can also be used for further enzyme-kinetic characterization of modulators, for example for determining the mechanism of inhibition, the rate of formation and dissociation of the enzyme-modulator complex or the energy consumptions associated with the formation and dissociation of the enzyme-modulator complex. The methods can additionally be employed advantageously according to the invention in the characterization of enzymes and enzyme reactions in which pyrophosphate is formed or consumed, including the characterization of substrate properties and the finding and optimization of surrogate substrates.

The advantages of the methods of the invention, especially the low susceptibility to interference from phosphate and ATP, can additionally be utilized in applications in the area of genome analysis and gene expression analysis. These applications are based on the detection and, where appropriate, the determination of the enzymatic activity of DNA- or RNA-dependent polymerases, including reverse transcriptases, with the aid of the methods of the invention; the use of embodiments with continuous luminescence measurement is of particular interest in these cases. Examples of possible uses in the area of genome analysis and gene expression analysis are nucleic acid sequencing (pyrosequencing) of DNA or RNA and the detection or measurement of nucleic acid amplifications by polymerase chain reaction (PCR).

The invention further relates to a chemical composition including dehydroluciferin, luciferin, ATP and luciferase which can be activated by pyrophosphate, e.g. luciferase from *Photinus pyralis*. The composition is, as already explained above, preferably configured as aqueous solution and may comprise additional components. The various and preferred possibilities for providing the composition, and the storage stability and the further manipulation have likewise already been explained hereinbefore.

The invention additionally relates to an assay kit for carrying out one of the methods described, which includes at least
  a suitable first container which comprises at least dehydroluciferin,
  a suitable second container which comprises at least luciferin,
  a suitable third container which comprises at least ATP,
  a suitable fourth container which comprises at least luciferase which can be activated by pyrophosphate, e.g. luciferase from *Photinus pyralis*.

Further assay kits of the invention for carrying out one of the methods described include at least
  one or more suitable containers which in each case comprise at least one or more components selected from the list consisting of dehydroluciferin, luciferin, ATP and luciferase which can be activated by pyrophosphate, e.g. luciferase from *Photinus pyralis*, with each listed component being present in at least one of the suitable containers.

The invention additionally relates to assay kits for carrying out one of the methods described, which include at least
  a suitable container which comprises at least dehydroluciferin, luciferin, ATP and luciferase which can be activated by pyrophosphate, e.g. luciferase from *Photinus pyralis*.

The listed components may in each case be present in combination with additional components: examples of additional components have already been described hereinbefore. The listed components or combinations of components are, if luciferase is not included, preferably present in the suitable containers as dry solid or dry solid mixture, for example as lyophilisate. If luciferase, e.g. luciferase from *Photinus pyralis* is included, the listed components or combinations of components are preferably present as aqueous solution with a glycerol content of from 10% to 60% proportion by volume, preferably 50% proportion by volume. To carry out one of the methods of the invention, the components and combinations of components present are, depending on the embodiment, put into aqueous solution or diluted with water, combined or contacted together and with the test sample, and measured.

Suitable containers are distinguished by good and long-term stability at temperatures, including rapid temperature changes, in the range from plus 20° C. to minus 80° C. Preferred containers are opaque and have an air- and water-tight closure of polymeric synthetic materials.

The assay kits of the invention may additionally comprise exemplary protocols for carrying out various embodiments of the methods of the invention, exemplary results, reference samples, literature references and further materials.

EXPLANATIONS OF THE FIGURES

Figure 2:
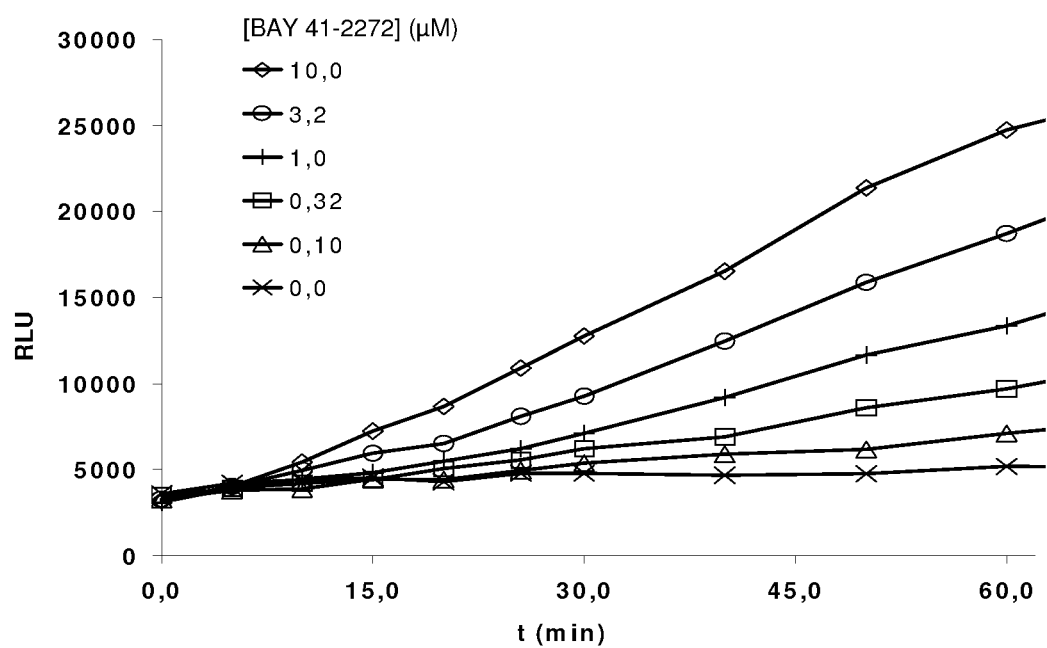
Figure 3:
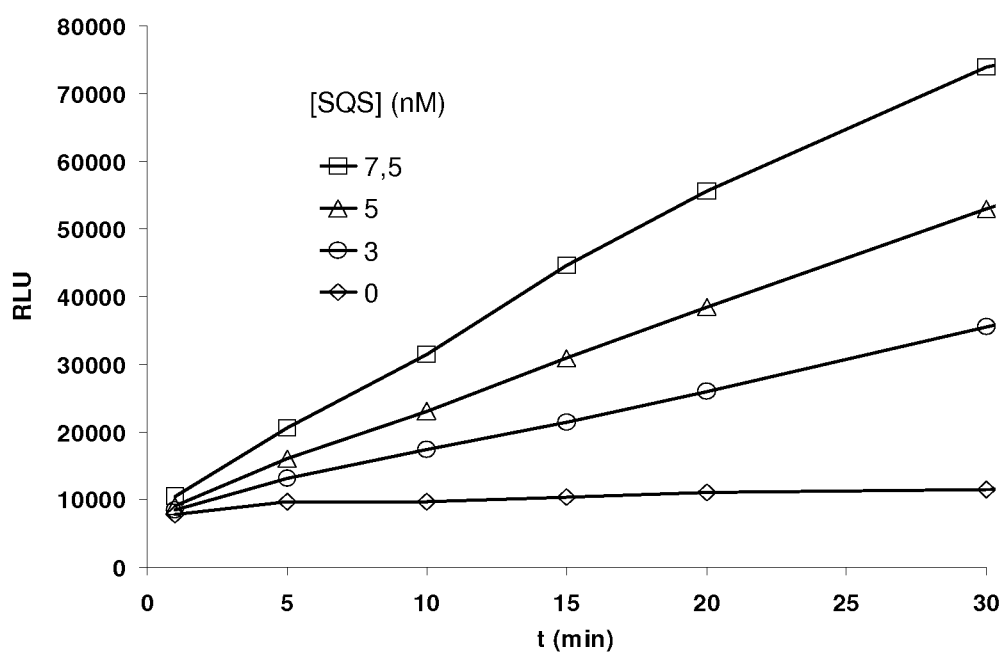
Figure 4:
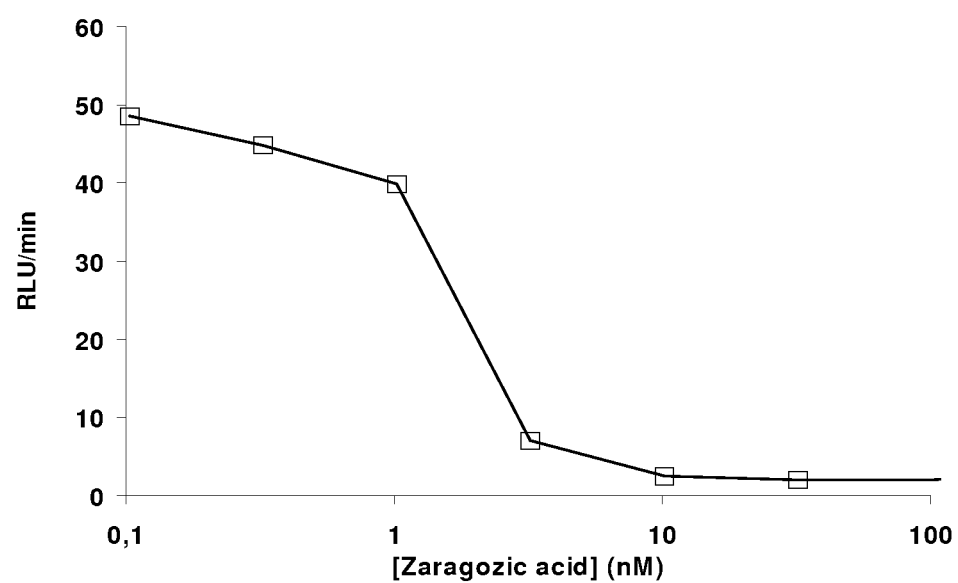

FIG. 1: measurement of a pyrophosphate concentration series; RLU, luminescence signal in relative luminescence units pyrophosphate], concentration of pyrophosphate, micromolar FIG. 2: measurement of the activation of soluble guanylyl cyclase (sGC) by various concentrations of BAY 41-2272; RLU, luminescence signal in relative luminescence units; t, incubation time in minutes; [BAY 41-2272], concentration of BAY 41-2272, micromolar FIG. 3: measurement of the activity of squalene synthase (SQS); RLU, luminescence signal in relative luminescence units; t, incubation time in minutes; [SQS], concentration of squalene synthase, nanomolar FIG. 4: measurement of the inhibition of squalene synthase by various concentrations of Zaragozic acid; RLU/min, change in the luminescence signal per unit time in relative luminescence units per minute; [zaragozic acid], concentration of zaragozic acid, nanomolar The invention is explained in more detail by the following examples:

EXAMPLE 1

Detection of Pyrophosphate

Pyrophosphate (PPi) is detected by the method of the invention. The signal produced in the assay increases with increasing PPi concentration (see FIG. 1).
Procedure for PPi Detection To carry out the PPi detection, 40 µl of PPi solution (Sigma; serial dilution in buffer: 50 mM TEA, 2 mM MgCl2, 0.1% BSA (fraction V), 0.005% Brij, pH 7.5) were introduced into a microplate. Subsequently, 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in buffer (50 mM TEA, 2 mM MgCl2, 0.1% BSA (fraction V), 0.005% Brij, pH 7.5) were added. The detection mixtures were measured in a luminometer at room temperature.

EXAMPLE 2

Measurement of sGC Enzyme Activity by Means of PPi Detection

Soluble guanylyl cyclase (sGC) converts on stimulation GTP into cGMP and pyrophosphate (PPi). PPi is detected with the aid of the method of the invention. The signal produced in the assay increases as the reaction progresses and serves as a measure of the sGC enzyme activity. It is possible with the aid of a PPi reference plot (compare Example 1) to characterize the enzyme in a known manner, e.g. in terms of conversion rate, stimulability or Michaelis constant.
Assay Procedure To carry out the assay, 29 µl of enzyme solution (0-10 nM soluble guanylyl cyclase (prepared according to Hönicka et al., Journal of Molecular Medicine 77 (1999) 14-23), in 50 mM TEA, 2 mM MgCl2, 0.1% BSA (fraction V), 0.005% Brij, pH 7.5) were introduced into the microplate, and 1 µl of the stimulator solution (0-10 µM DEA NONOate (Alexis) in DMSO) was added. The mixture was incubated at room temperature for 10 min. Then 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM MgCl2, 0.1% BSA (fraction V), 0.005% Brij, pH 7.5) were added. The enzyme reaction was started by adding 20 µl of substrate solution (1.25 mM guanosine 5'-triphosphate (Sigma) in 50 mM TEA, 2 mM MgCl2, 0.1% BSA (fraction V), 0.005% Brij, pH 7.5) and measured continuously in a luminometer.

EXAMPLE 3

Characterization of Test Substances for Stimulation of sGC Enzyme Activity

Soluble guanylyl cyclase (sGC) converts on stimulation GTP into cGMP and pyrophosphate (PPi). PPi is detected with the aid of the method of the invention. The signal produced in the assay increases as the reaction progresses and serves as a measure of the sGC enzyme activity under the given stimulation (see FIG. 2).
Assay Procedure:

To carry out the assay, 29 µl of enzyme solution (0-10 nM soluble guanylyl cyclase (prepared according to Hönicka et al., Journal of Molecular Medicine 77 (1999) 14-23), in 50 mM TEA, 2 mM MgCl2, 0.1% BSA (fraction V), 0.005% Brij, pH 7.5) were introduced into the microplate, and 1 µl of the substance to be tested (e.g. BAY 412272 (Alexis) serially diluted in DMSO) was added. The mixture was incubated at room temperature for 10 min. Then 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM MgCl2, 0.1% BSA (fraction V), 0.005% Brij, pH 7.5) were added. The enzyme reaction was started by adding 20 µl of substrate solution (1.25 mM guanosine 5'-triphosphate (Sigma) in 50 mM TEA, 2 mM MgCl2, 0.1% BSA (fraction V), 0.005% Brij, pH 7.5) and measured continuously in a luminometer. The extent of the stimulation by the substance to be tested can be determined relative to the signal of the unstimulated reaction.

EXAMPLE 4

Measurement of SQS Enzyme Activity by Means of PPi Detection

Squalene synthase (SQS) converts farnesyl pyrophosphate in the presence of NADPH into squalene and pyrophosphate (PPi). PPi is detected with the aid of the method according to the invention. The signal produced in the assay increases as the reaction progresses and serves as a measure of the SQS enzyme activity (see FIG. 3). The enzyme can be characterized in a known manner, e.g. in terms of conversion rate or Michaelis constant, with the aid of a PPi reference plot (compare Example 1).
Assay Procedure:

To carry out the assay, 40 µl of enzyme solution (0-10 nM SQS (prepared according to Soltis, Arch. Biochem. Biophys. 316 (1995) 713) in 50 mM Tris, 5 mM MgCl2, 1.5 mM glutathione, 5 mM CHAPS, pH 7.5) were introduced into the microplate. Then 20 µl of detection mix (1.3 nM Firefly Luciferase (*Photinus pyralis* luciferase, Promega), 35 µM dehydroluciferin (prepared according to Bitler & McElroy, Arch. Biochem. Biophys. 72 (1957) 358), 140 µM luciferin (Promega), 175 µM ATP (Sigma) and 0.5 mM DTT (Sigma) in 50 mM Tris, 5 mM MgCl2, 5 mM CHAPS, 0.02% BSA (fraction V), pH 7.5) were added. The enzyme reaction was started by adding 20 µl of substrate solution (10.5 µM farnesyl pyrophosphate (Sigma), 150 µM NADPH (Sigma) in 50 mM Tris, 5 mM MgCl2, 5 mM CHAPS, pH 7.5) and continuously measured in a luminometer.

EXAMPLE 5

Characterization of Test Substances in Terms of Inhibition of SQS Enzyme Activity Squalene synthase (SQS) converts farnesyl pyrophosphate in the presence of NADPH into squalene and pyrophosphate (PPi). PPi is detected with the aid of the method according to the invention. The signal produced in the assay increases as the reaction progresses and serves as a measure of the SQS enzyme activity with the given inhibition (see FIG. 4).

Assay Procedure:

To carry out the assay, 39 µl of enzyme solution (0-10 nM SQS (prepared according to Soltis, Arch. Biochem. Biophys. 316 (1995) 713) in 50 mM Tris, 5 mM MgCl2, 1.5 mM glutathione, 5 mM CHAPS, pH 7.5) were introduced into the microplate, and 1 µl of the test substance solution (serial dilution in DMSO) was added. The mixture was incubated at room temperature for 10 min. Then 20 µl of detection mix (1.3 nM Firefly Luciferase (*Photinus pyralis* luciferase, Promega), 35 µM dehydroluciferin (prepared according to Bitler & McElroy, Arch. Biochem. Biophys. 72 (1957) 358), 140 µM luciferin (Promega), 175 µM ATP (Sigma) and 0.5 mM DTT (Sigma) in 50 mM Tris, 5 mM MgCl2, 5 mM CHAPS, 0.02% BSA (fraction V), pH 7.5) were added. The enzyme reaction was started by adding 20 µl of substrate solution (10.5 µM farnesyl pyrophosphate (Sigma), 150 µM NADPH (Sigma) in 50 mM Tris, 5 mM MgCl2, 5 mM CHAPS, pH 7.5) and continuously measured in a luminometer. The extent of the inhibition can be determined relative to the signal of the uninhibited reaction.

The possible test substance-mediated inhibition of luciferase activity can be examined as follows:

After completion of the luminometer measurement, 20 µl of a PPi-containing control solution (5 µM PPi (Sigma), 0.02% BSA (fraction V, Sigma), 44 µM ATP (Sigma), 35 µM luciferin (Promega), 0.4 nM Firefly Luciferase (*Photinus pyralis* luciferase, Promega), 6 µM dehydroluciferin (prepared according to Bitler & McElroy, Arch. Biochem. Biophys. 72 (1957) 358) in 50 mM Tris, 2 mM MgCl2, pH 8) are added, and again measured in the luminometer.

If the increment in the signal generated by addition of the PPi-containing control solution in an inhibited reaction mixture is as large as in an uninhibited control mixture, inhibition of the luciferase reaction can be ruled out.

The invention claimed is:

1. A method for detecting pyrophosphate, comprising the steps of:
   (a) incubating a composition consisting essentially of dehydroluciferin, ATP, and luciferase which is activated by pyrophosphate, to make an incubated composition, the ATP being present in an amount that is in excess of the dehydroluciferin and luciferase,
   (b) combining the incubated composition with luciferin to make a detection mix, the luciferin being present in an amount that is in excess of the dehydroluciferin and luciferase,
   (c) contacting a test sample with the detection mix, and
   (d) measuring luminescence of the test sample, whereby pyrophosphate concentration in the test sample is determined by the intensity of the luminescence.

2. The method as claimed in claim 1, where the luciferase is selected from the group consisting of:
   a non-recombinant or recombinant luciferases,
   a non-recombinant or recombinant luciferase from insects of the superfamilies Elateroidea and Cantharoidea,
   a non-recombinant or recombinant luciferase from the insects *Photinus pyralis, Pyrophorus plagiophthalamus, Luciola cruciata, Luciola lateralis* or *Luciola mingrelica,*
   a luciferase derived or mutated from any of the above luciferases, and
   a mixture of two or more of the above luciferases.

3. The method as claimed in claim 1, wherein the test sample originates from a natural source including the animate and inanimate environment.

4. The method as claimed in claim 1, wherein the test sample originates from a vegetable or animal organism.

5. The method as claimed in claim 1, wherein the test sample originates from the human body.

6. The method as claimed in claim 5, wherein the test sample comprises samples or preparations of tissue or body fluids.

7. A method for measuring the time course of a pyrophosphate-forming or consuming a chemical or enzyme reaction, comprising the steps of:
   (a) providing a mixture in which pyrophosphate is being formed or consumed in a chemical or enzyme reaction;
   (b) adding a detection mix to the mixture, the detection mix comprising an incubated composition consisting essentially of dehydroluciferin, ATP, and a luciferase which can be activated by pyrophosphate, the detection mix further comprising luciferin, the ATP and luciferin being present in an amount that is in excess of the dehydroluciferin and luciferase; and
   (c) continuously measuring luminescence of the mixture during the chemical or enzyme reaction, pyrophosphate concentration in the test sample is determined by the intensity of the luminescence.

8. A method for measuring the time course of a chemical or enzyme reaction that forms or consumes pyrophosphate comprising the steps of:
   (a) providing a mixture that can form or consume pyrophosphate in an chemical or enzyme reaction, the mixture comprising a detection mix consisting essentially of an incubated composition of dehydroluciferin, ATP, and a luciferase which can be activated by pyrophosphate, the detection mix further comprising luciferin, the ATP and luciferin being present in an amount that is in excess of the dehydroluciferin and luciferase;
   (b) starting a chemical or enzyme reaction in the mixture by adding a substrate to the mixture; and
   (c) continuously measuring luminescence of the mixture during the chemical or enzyme reaction, pyrophosphate concentration in the test sample is determined by the intensity of the luminescence.

9. The method as claimed in claim 7 or 8, where the luciferase is selected from the group consisting of:
   a non-recombinant or recombinant luciferase,
   a non-recombinant or recombinant luciferase from insects of the superfamilies Elateroidea and Cantharoidea, a non-recombinant or recombinant luciferase from the insects *Photinus pyralis, Pyrophorus plagiophthalamus, Luciola cruciata, Luciola lateralis* or *Luciola mingrelica*, a luciferase derived or mutated from any of the above luciferases, and a mixture of two or more of the above luciferases.

10. The method as claimed in claim 7 or 8, where the chemical or enzyme reaction is selected from the group consisting of:

pyrophosphate-forming or pyrophosphate-consuming enzyme reactions, guanylyl cyclase-catalyzed reactions, adenylyl cyclase-catalyzed reaction, squalene synthase-catalyzed reaction, pyrophosphatase-catalyzed reaction, DNA polymerase-catalyzed reaction, and RNA polymerase-catalyzed reaction.

11. The method as claimed in claim 7 or 8, characterized in that the enzyme reaction is catalyzed by soluble vascular guanylyl cyclase.

* * * * *